United States Patent
Sawai

(10) Patent No.: US 6,719,031 B2
(45) Date of Patent: Apr. 13, 2004

(54) DEVICE FOR CUTTING OUT AN ARTICLE FROM A LONG TAPE AND ADHERING THE ARTICLE TO AN ADHESIVE TAPE

(75) Inventor: Seiichi Sawai, Fukushima (JP)

(73) Assignee: Johnson & Johnson Kabushiki Kaisha (JP)

(*) Notice: Subject to any disclaimer, the term of this patent is extended or adjusted under 35 U.S.C. 154(b) by 16 days.

(21) Appl. No.: 10/253,253

(22) Filed: Sep. 24, 2002

(65) Prior Publication Data

US 2003/0089210 A1 May 15, 2003

(30) Foreign Application Priority Data

Sep. 28, 2001 (JP) .......................................... 2001-303824

(51) Int. Cl.$^7$ ............................................... B32B 31/00
(52) U.S. Cl. ........................ 156/519; 156/552; 156/556; 156/567; 271/91; 271/94; 271/196; 198/471.1; 198/803.5
(58) Field of Search ................................. 156/519, 520, 156/517, 516, 264, 265, 269, 270, 297, 552, 556, 558, 566, 567, 568; 271/91, 94, 95, 98, 99, 196; 269/21; 198/471.1, 803.5

(56) References Cited

U.S. PATENT DOCUMENTS

| 3,879,246 A | * | 4/1975 | Walker ........................ 156/265 |
| 4,664,736 A | * | 5/1987 | Faasse, Jr. .................. 156/264 |
| 4,726,876 A | * | 2/1988 | Tomsovic, Jr. ............... 156/552 |

* cited by examiner

Primary Examiner—Richard Crispino
Assistant Examiner—Cheryl N. Hawkins

(57) ABSTRACT

Device for cutting out articles from a long tape and adhering the articles to an adhesive tape comprises a cutting roll, an adhering roll and a transfer device for transferring the cut-out articles to the adhesive tape. The cutting roll carries blade forms for cutting out the articles. The adhering roll carries anvils whose shapes correspond to the shape of the blades. The adhering roll also carries cylinders each of which is disposed adjacent an anvil and has a shaft capable of piston action disposed therein. Each shaft has a suction mouth at its end. The suction mouths are used to transfer the cut-out articles from the cutting roll to the adhesive tape to which they are to be adhered.

4 Claims, 3 Drawing Sheets

[Fig. 1]
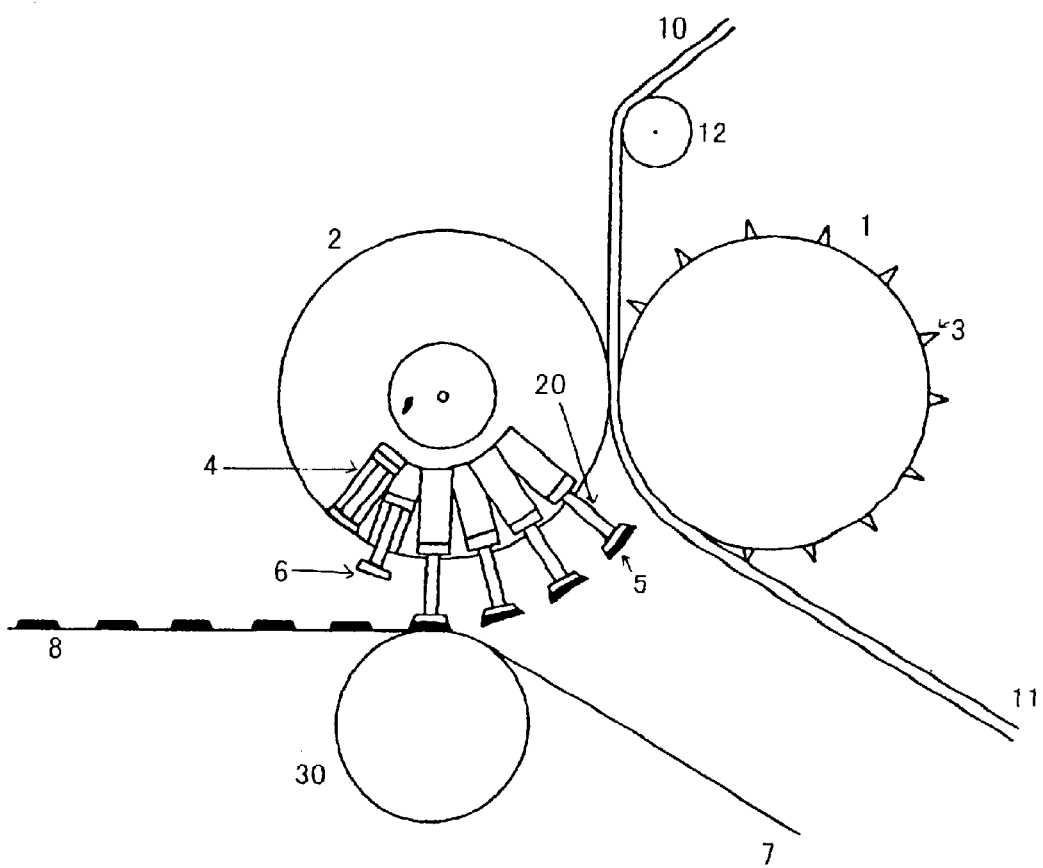

[Fig. 2]
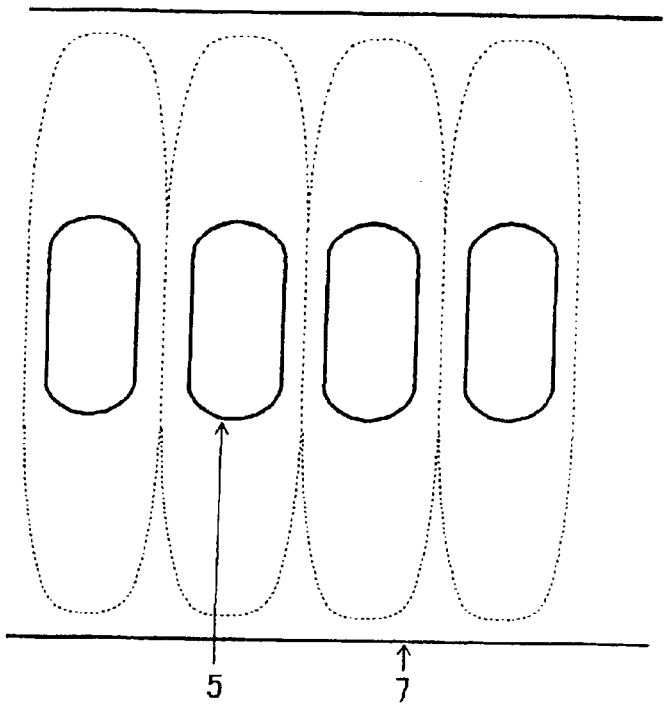
5  7
[Fig. 3]
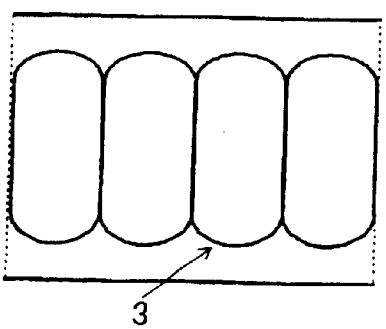
3
[Fig. 4]
(a)  (b)  (c)
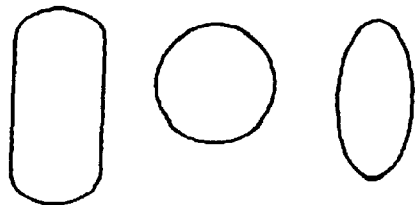

[Fig. 5]
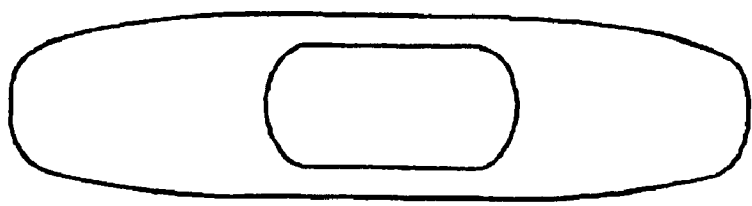
[Fig. 6]
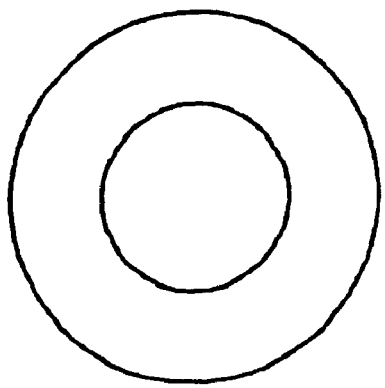
[Fig. 7]
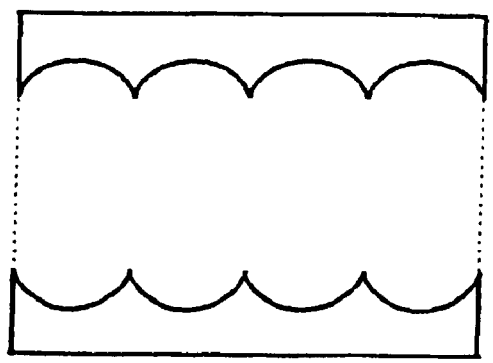
11

DEVICE FOR CUTTING OUT AN ARTICLE FROM A LONG TAPE AND ADHERING THE ARTICLE TO AN ADHESIVE TAPE

DETAILED DESCRIPTION OF THE INVENTION

1. Technical Field of the Invention

The present invention relates to a device for cutting out an article from a long tape and adhering the article on an adhesive tape. Further the present invention relates to a device for cutting and adhering pads having a variety of shapes, in particular, to a compact device for cutting and adhering capable of mass production of a pad without occupying a large area or volume for setting. The device of the present invention for cutting and adhering a pad is, in particular, suitable for cutting and adhering a pads for dressing, adhesive bandage and the like.

2. Prior Art

Conventionally a process of cutting out an article from a long tape and a process of adhering the article to an adhesive tape are separately carried out using different devices. Respective processes are intermittently carried out, intermittent actions are recurred rapidly, which limits the transfer rate and also a number of cum mechanisms and the like recurring intermittent action are used and mechanical vibrations and noises are unavoidable, large mechanical stresses are loaded on members of frameworks, distortion is apt to occur and a lot of works are unavoidable for check-out, maintenance and repair works. A variety of continuous production systems have been devised to eliminate such defects associated with intermittent processes. For example, a production device of adhesive bandage sequentially producing adhesive bandage by combining a number of rolls (Laid-Open Patent No. 255061/1988), a continuous production device of adhesive bandage including a process of cutting a pad and a process of sequentially adhering the pad at predetermined intervals (Laid-Open Patent No. 97453/1989), a continuous production device of adhesive bandage including a process of cutting an adhesive bandage using a rotary die cutter and a process of sequentially delivering the cut adhesive bandage to a transfer machine while holding the adhesive bandage by suction (Laid-Open Patent No. 97454/1989), a continuous method and device for adhering a pad to an adhesive film including processes comprising receiving a pad which has been cut in predetermined dimensions at a pad receiving position and broadening a spacing between adjacent pads by continuously accelerating transferring rate during continuous transfer of the pad aligned in a predetermined orientation (Laid-Open Patent No. 98557/1989), a continuous method and device for adhering pad to adhesive film including processes comprising receiving a pad which has been cut in a predetermined dimension at a pad receiving position and continuously transferring a pad at a constant rate and adhering the pad to an adhesive surface of a long adhesive tape which moves faster than the pad transfer speed (Laid-Open Patent No. 98557/1989), a continuous method and device for adhering a pad to a long adhesive film including processes comprising transferring a pad which has been cut at predetermined dimensions at a constant rate while holding the pad by sucking arranged at a spacing corresponding to a distance between adjacent pad adhering position on an adhesive film, approaching the pad to an adhesive surface of the long adhesive film moving at nearly the same rate as that of the pad, and stopping suction of the pad at the approaching position (Laid-Open Patent No. 144486/1989) and an adhesive dressing pad production module and an adhesive dressing pad production method comprising a module-type apparatus of which each module is freely detachable and maintenance is easy wherein the pad is accurately and quickly cut out and transferred to the adhesive surface of the dressing (Laid-Open Patent No. 2001-204758) are known.

Further in conventional production of dressings and adhesive bandages, to avoid complication of processes and to use materials economically, adhesive bandages were produced by adhering a long pad material tape having a width several times shorter than that of a long adhesive tape which is manufactured by coating an adhesive on a base sheet of a long tape to a central part of the long adhesive tape in a longitudinal direction of the long adhesive tape, cutting the long tape in the shape of the adhesive bandage so that the pad is positioned at a central part, or by making a pad by simply cutting a long tape and adhering the pad on adhesive surface of the adhesive bandage. Former type of the pad is known as "whole width pad", latter method is called "cut and place method", in this method it is possible to make the whole width pad however by making the pad width narrower than that of the adhesive tape, the pad can be surrounded by the adhesive layer. This type of pad is known as "island pad".

PROBLEMS THIS INVENTION SEEKS TO SOLVE

The whole width pad is simple in structure and easy to manufacture and widely used in related industrial world, however contamination of pad from outside or leak of permeated body fluid from wounded part to outside is apt to occur because there is no adhesive layer in lateral sides of the pad. The island pad can be formed in various design products, however it takes comparatively long time for production and arrangement of the pad is apt to be inaccurate. On the other hand, when a pad is formed by simply cutting a long tape with a linear blade, the pad shape for mass production is limited to square or rectangle, and in the case of shapes such as round or oval shape, disposal of waste part is unavoidable, a specific blade for cutting is necessary, which increases production costs and more accuracy is needed in production processes than conventional methods, a yield ratio becomes low, a severer production process control than conventional one is demanded so that the waste does not get mixed in final product, contaminate or stick to an adhesive surface of a product, which causes the product comparatively expensive. Also because cutting of an article and adhesion of the article to an adhesive surface of an long adhesive tape are usually carried out by different devices, two or more devices must be installed and they occupy a large area or volume, and a lot of works for checkout and maintenance and also for adjustment between those devices such as timing or positioning are unavoidable. Consequently development of a device which performs both cutting of an article and adhering of the article to an adhesive surface of a long adhesive tape is desired without decreasing production efficiency when producing various shapes of article.

MEANS FOR SOLVING THE PROBLEMS

The present invention relates to a device for cutting out an article from a long tape and adhering the article to an adhesive tape comprising: a cutting roll having blade molds on the roll surface for cutting out an article by holding and pressing a long tape between the roll and an adhering roll; the adhering roll having anvils of which shapes correspond to those of the mold blades of the cutting roll and cylinders each having a shaft capable of piston action having suction mouth protrudable from the roll surface wherein the cylinder is disposed in each anvil shape; and a transfer device for an adhesive tape to which the articles are adhered, wherein the shaft is contained in the cylinder before sucking the article and when reaching predetermined position on the adhesive tape to which the article is adhered the cylinder adheres the article to the adhesive tape in protruding state while sucking the article. And also the present invention relates to a device for cutting out a pad from a long tape and adhering the pad to an adhesive tape comprising: a cutting roll having blade molds on the roll surface for cutting out a pad by holding and pressing a long tape between the cutting roll and an adhering roll; the adhering roll having a number of cylinders on the roll surface wherein respective cylinders have shafts protrudable from the roll surface and having a suction mouth for sucking the pad wherein each cylinder is disposed corresponding to each shape of the pad to be cut; and a transfer device of an adhesive tape on which the pad is adhered, wherein the shaft is contained in the cylinder before sucking the pad and adheres the pad in protruding state while sucking the pad when reaching predetermined position on the adhesive tape to which the pad is adhered, and further the device for cutting and adhering the pad wherein the sucking mouth is contained in the cylinder by vacuum after the protruded shaft adheres the pad, and also the device for cutting and adhering the pad according to Claim 2 or 3 wherein the adhering roll is synchronized with the transfer device of the adhesive tape.

The article in the present invention includes all kind of material used by adhering to an adhesive tape such as a pad for an adhesive bandage and dressing for wound, a water-absorbing material for disposable diaper. The pad in this invention is a material of adhesive bandage, dressing and the like for covering wound surface, absorbing body fluid such as permeated blood, protecting the wound surface and keeping clean, sterilizing or treating with pharmaceutical drugs. The pad is composed of woven fabrics, nonwoven fabrics, water-absorbable materials or composite materials thereof made of various fibers such as cotton and synthetic fibers and in the present invention the pad is cut out of a long tape.

The principal part of the device of the present invention is composed of a combination of two rolls, a cutting roll and an adhering roll. Two rolls rotate synchronously so that the velocities of the outer surfaces of both rolls become identical. The cutting roll has blade molds around the roll outer surface to cut out articles. Anvil surfaces are formed around the outer surface of the adhering roll at positions corresponding to the blade mold positions. When a long tape of an article material is fed, two rolls rotate at a rate corresponding to that of the tape and send out the tape. The contact point of the knife edge of the blade mold and the anvil is the contacting point of two rolls and the blade mold cuts out an article in the shape of the mold from the long tape. Consequently by altering the blade mold shape into circle, oval shape or the like, an article in the shape other than tetragon may be easily produced.

In the present invention, as the tape after cutting out the articles is still continuous at both sides and may be disposed of as it is from the process using a tape take-up machine, no fine fragment of pad material or fiber is formed which can contaminate the product. A shaft protrudable from the outer surface of the adhering roll is arranged inside the anvil surface. The top of said shaft has an air suction mouth connected to a decompressor which holds an article by sucking the air from the start of cutting the article until adhering the article to an adhesive surface of an adhesive tape.

An adhesive tape transfer machine is located adjacent to the adhering roll and transfers the adhesive tape which is formed by coating an adhesive on a side of the base sheet of the adhesive bandage toward the transfer roll at a constant rate. The shaft holding the article begins to protrude out of the outer surface of the roll by air pressure or centrifugal force due to the roll rotation and reaches a predetermined distance from the outer surface. The air pressure at the time is from 0.2 kg/cm2 to 1 kg/cm2. The predetermined distance of the shaft protrusion is set so that the article may reach the adhesive surface of the adhesive tape on the transferring machine, and as the roll rotates the article at the end of the shaft, the article approaches to the adhesive surface of the adhesive tape on the transferring machine to adhere the article to the adhesive surface. The adhering roll and the adhesive tape transferring machine is synchronized with each other to control where the article should be attached to the adhesive tape. Consequently spacing distance between adjacent pads on the adhesive surface of the adhesive tape may be easily controlled or altered by changing the ratio of the revolution rate of the adhering roll to the transfer rate of the adhesive tape transfer machine. This facilitates change in spacing distance between adjacent articles when adhering a comparatively small pad to a central part of a wide adhesive surface and the like. In this regard, the system of the present invention is effective when the distance between articles adhered on the adhesive tape is made longer than the distance between articles when they are cut out. This is because the transfer rate of articles at the air suction mouth can be made identical with the transfer rate of the adhesive tape when the ratio of the distance between articles when the articles are cut out to the distance between the articles on the adhesive tape is made identical with the ratio of the radius of the adhering roll to the radius at the position of the air suction mouth when the shaft is protruded. Thereby defects such as wrinkles and bendings of article or adhesive tape which are caused by the difference of transfer rates between articles and adhesive tape. Consequently when the distance between adjacent articles adhered is made longer, the ratio of the shaft protrusion distance to the radius of the adhering roll should be made larger to match the transfer rate of articles to that of the adhesive tape.

After adhering the article, the air suction from the suction mouth of the shaft is stopped and the shaft is drew back into the cylinder in the roll. Then reaching again the contact point with the cutting roll in the state the shaft is drew back, the processes of article cutting and adhering are finished and the processes are repeated.

As described above in the present invention, processes of cutting an article and adhering the article to an adhesive surface are both completed during a rotation of the adhering roll. The roll revolution rate is continuous and constant during rotations and no excessive stress is loaded on the devices. Consequently downsizing of the system, easy maintenance, efficient manufacturing and cost reduction are realized and the amount of production is increased by enhancing the roll revolution rates.

The present invention is further described in detail while referring drawings.

WORDING FORM OF THE INVENTION

FIG. 1 is a front view of the first Example of the device of the present invention. In this Example, the present invention is described in the case of a pad of an adhesive bandage as an example of the article. A long tape 10 of composite material laminating Delnet (registered trademark) and a nonwoven fabric made of SBS-type block copolymer is used for the pad material tape. The width of the tape 10 is 35 mm and the thickness is 1 mm. In the drawing, the tape 10 is provided from above to the contact point, that is, to the cutting point, of cutting roll 1 and adhering roll 2. The radius of the cutting roll 1 is 300 mm, each shape of the blade mold on the outer surface of the roll is identical to that of the pad 5 in FIG. 2 and 140 molds are aligned on the outer surface.

An example of the alignment of the blade mold is shown in FIG. 3. The pad of FIG. 3 has parallel linear parts of 20 mm length at the central part of the pad in longitudinal direction and half approximate oval shapes in the shape shown by the figure are attached to the linear parts respectively. A blade constructs a parallel linear part of adjacent pad in common, and two half approximate oval shape parts are attached to both sides thereof. An angle of the blade top is 30° to 90°, preferably 40° to 80°, and more preferably 50° to 70°. In case less than 30°, the blade becomes easy to wear and shortens the blade life. On the other hand in case exceeding 90°, it is necessary to increase load pressure to the adhering roll to cut and no sharp cutting surface may be formed. It is preferred to arrange the inside angle, that is to say, an angle formed by the pad material tape surface and the inside blade wall near to perpendicular.

The pressing pressure of cutting roll against adhering roll is 1 to 3 kg/cm$^2$. If the pressure is less than 1 kg/cm$^2$, the blade sometimes will not cut out the pad accurately. If exceeding 3 kg/cm$^2$, the blade will soon be worn and it hinders a long-time continuous operation.

FIG. 7 shows a shape of the pad material tape after pads are cut. In the drawing, the central area compartmentalized by the dotted lines at both upper and lower sides in the longitudinal direction is a hole formed by cutting out pads, and the rest areas partitioned by the both sides of the tape are remained waste parts of the long tape after cutting out pads, which continue for long distance as shown in 11 in FIG. 1 and they are wound up and disposed of. Therefore no smaller waste of the tape material is formed.

The radius of the adhering roll is 300 mm the same as that of the cutting roll. Consequently both rolls are synchronously driven at same rotation rate. The width of the anvil face is 1 mm and each anvil is arranged so as to correspond to each blade mold of the cutting roll. The position of the blade mold and anvil face always coincide with each other because both rolls are driven synchronously. Cylinder 4 shown in FIG. 1 is arranged inside the cutting roll in the surface area surrounded by the anvil face. For the smooth adhesion of the pad without excessive stresses on the shaft, it is preferred to adjust the central axis of the cylinder in the longitudinal direction on the straight line passing through central line of the adhering roll rotation axis. Outer diameter of cylinder is 10 mm and piston connected to the shaft moves reciprocally in the cylinder. When the pad width is so small, it happens that cylinders cannot be aligned on a same circle because adjacent cylinders come close to each other as they come near to roll rotation axis since cylinder has a same diameter along longitudinal direction. In such case, cylinders can be arranged in zig-zag pattern instead of aligning on a circle along the rotation direction of the adhering roll.

At the central part of the shaft of axial direction, an air suction path is formed and connected to an air suction apparatus. The air suction path is connected to the pad suction mouth opened in central part of the shaft surface to hold a pad by suction.

The shaft is hidden inside the cylinder by reducing air pressure in the piston room after adhering a pad. The bottom of the cylinder is connected to the air suction apparatus.

The pad suction mouth for holding a pad is positioned at the same level as the anvil surface when the shaft is contained in the cylinder. The suction mouth is positioned in central area of the shaft face. The cylinder and shaft are constructed as shown in FIG. 1 and the shaft is contained in the cylinder before the pad is cut. After the pad is cut, the air is sucked from the suction mouth of the shaft and the pad is held by suction on the shaft face. The shaft begins to protrude out of the adhering roll surface as the roll rotates. When the shaft reaches the adhesive surface of the adhesive tape 7 on the adhering roll surface and completes the adhesion of the pad to the adhesive tape, the suction from the suction mouth is stopped, concurrently the shaft begins to enter into the cylinder by reduced pressure, the shaft face returns to the level of the adhering roll surface and the pad cutting operation is ready.

The adhesive tape 7 to which a pad is to be adhered is a long tape of a bandage base sheet on a side of which an adhesive is coated. The adhesive tape 7 is transferred by the adhesive tape transfer machine and a pad is attached thereto on the tape support roll 30 as shown in FIG. 1.

EFFECT OF THE INVENTION

As described above, the article cutting and adhering device of the present invention may easily produce articles with a number of shapes other than conventional tetragons and the like and complete cutting and adhering of the articles to the adhesive surface of the bandage in one operation. Consequently the device of the present invention is in particular preferred to produce island pads and may easily set and alter spacing between adjacent pads on an adhesive tape by changing the ratio of the adhering roll rotation rate to the transfer rate of the adhesive tape transfer machine.

BRIEF DESCRIPTION OF DRAWINGS

FIG. 1 is a descriptive drawing showing the structure of the article cutting and adhering device of the present invention.

FIG. 2 is a descriptive view showing the state where a pad is attached to a long adhesive tape in cutting and adhering device of the present invention.

FIG. 3 is a descriptive view showing the arrangement of cutting blade in the cutting and adhering device of the present invention.

FIG. 4 is examples of the pad shapes of the present invention.

FIG. 5 is an example of adhesive bandage produced according to the present invention.

FIG. 6 is another example of adhesive bandage produced according to the present invention.

FIG. 7 is a shape of an article material tape after articles are cut our in the present invention.

DESCRIPTION OF SYMBOLS 1 cutting roll, 2 adhering roll, 3 blade mold, 4 cylinder, 5 pad, 6 suction mouth, 7 adhesive tape, 8 adhesive tape transfer machine, 10 pad material tape, 11 tape after cutting article, 20 shaft, 30 tape support roll

What is claimed is:
1. A device for cutting out an article from a long tape and adhering the article to an adhesive tape comprising:

a cutting roll having blade molds on the roll surface for cutting out an article by holding and pressing a long tape between the roll and an adhering roll;

the adhering roll having anvils of which shapes correspond to those of the mold blades of the cutting roll and cylinders each having a shaft capable of piston action having suction mouth protrudable from the roll surface wherein the cylinder is disposed in each anvil shape; and a transfer device for an adhesive tape to which the articles are adhered, wherein the shaft is contained in the cylinder before sucking the article and when reaching predetermined position on the adhesive tape to which the article is adhered the cylinder adheres the article to the adhesive tape in protruding state while sucking the article.

2. A device for cutting out a pad from a long tape and adhering the pad to an adhesive tape comprising:

a cutting roll having blade molds on the roll surface for cutting out a pad by holding and pressing a long tape between the cutting roll and an adhering roll;

the adhering roll having a number of cylinders on the roll surface wherein respective cylinders have shafts protrudable from the roll surface and having a suction mouth for sucking the pad wherein each cylinder is disposed corresponding to each shape of the pad to be cut; and a transfer device of an adhesive tape on which the pad is adhered, wherein the shaft is contained in the cylinder before sucking the pad and adheres the pad in protruding state while sucking the pad when reaching predetermined position on the adhesive tape to which the pad is adhered.

3. The device for cutting and adhering the pad according to claim 2 wherein the sucking mouth is contained in the cylinder by vacuum after the protruded shaft adheres the pad.

4. The device for cutting and adhering the pad according to claim 2 wherein the adhering roll is synchronized with the transfer device of the adhesive tape.

* * * * *